United States Patent
Lazzara et al.

[11] Patent Number: 6,155,828
[45] Date of Patent: Dec. 5, 2000

[54] EMERGENCE PROFILE SYSTEM HAVING A COMBINED HEALING ABUTMENT AND IMPRESSION COPING

[75] Inventors: Richard J. Lazzara, Lake Worth; Keith D. Beaty, Jupiter; Ralph E. Goodman, West Palm Beach, all of Fla.

[73] Assignee: Implant Innovations, Inc., Palm Beach Gardens, Fla.

[21] Appl. No.: 09/218,794

[22] Filed: Dec. 21, 1998

Related U.S. Application Data

[63] Continuation of application No. 08/789,413, Jan. 29, 1997, Pat. No. 5,873,722.
[60] Provisional application No. 60/010,603, Feb. 2, 1996, and provisional application No. 60/026,859, Sep. 30, 1996.

[51] Int. Cl.[7] .................................................... A61C 8/00
[52] U.S. Cl. ......................... 433/173; 433/172; 433/213
[58] Field of Search .................................. 433/172, 173, 433/174, 213, 214

[56] References Cited

U.S. PATENT DOCUMENTS

| | | |
|---|---|---|
| 3,958,471 | 5/1976 | Müller . |
| 4,011,602 | 3/1977 | Rybicki et al. . |
| 4,177,562 | 12/1979 | Miller et al. . |
| 4,547,157 | 10/1985 | Driskell . |
| 4,624,673 | 11/1986 | Meyer . |
| 4,713,004 | 12/1987 | Linkow et al. . |
| 4,758,161 | 7/1988 | Niznick . |
| 4,772,204 | 9/1988 | Söderberg . |
| 4,850,870 | 7/1989 | Lazzara et al. . |
| 4,850,873 | 7/1989 | Lazzara et al. . |
| 4,856,994 | 8/1989 | Lazzara et al. . |
| 4,872,839 | 10/1989 | Brajnovic . |
| 4,955,811 | 9/1990 | Lazzara et al. . |
| 4,988,297 | 1/1991 | Lazzara et al. . |
| 4,988,298 | 1/1991 | Lazzara et al. . |

(List continued on next page.)

FOREIGN PATENT DOCUMENTS

| | | |
|---|---|---|
| 0 657 146 A1 | 6/1995 | European Pat. Off. . |
| 2 114 323 | 10/1971 | Germany . |
| 3 531 389 A1 | 3/1987 | Germany . |
| 4 028 855 | 3/1995 | Germany . |
| 679117 A5 | 12/1991 | Switzerland . |
| 1 291 470 | 10/1972 | United Kingdom . |
| WO 85/02337 A1 | 6/1985 | WIPO . |

OTHER PUBLICATIONS

"1989 Core–Vent Implant Symposium," Core–Vent Corporation, Mar. 1988 (2 pages).

(List continued on next page.)

*Primary Examiner*—Nicholas D. Lucchesi
*Attorney, Agent, or Firm*—Jenkens & Gilchrist

[57] ABSTRACT

A dental component attaches to an implant implanted in living jawbone having overlying gingiva. The implant has an apical end embedded within the jawbone and a gingival end near an interface of the gingiva and the jawbone. The dental component comprises a body having a lower region, a gingival region, and a supragingival region. The lower region has an end surface to engage the gingival end of the implant. The gingival region extends through the gingiva and has an outer surface for forming and maintaining an aperture in the gingiva that exposes the gingival end of the implant. The supragingival region has a top surface projecting above the gingiva. The dental component includes first means for receiving a healing element and second means for receiving an impression element. The healing element includes means for fastening the body to the implant so as to allow the gingiva to heal around the body for an extended period of time thereby forming the aperture. The impression element includes an upper segment extending above the supragingival region for receiving impression material and means for securing the body to the implant. Consequently, the dental component serves as part of both a gingival healing component and an impression component.

38 Claims, 15 Drawing Sheets

U.S. PATENT DOCUMENTS

| | | |
|---|---|---|
| 5,006,069 | 4/1991 | Lazzara et al. . |
| 5,030,096 | 7/1991 | Hurson et al. . |
| 5,035,619 | 7/1991 | Daftary .................................. 433/173 |
| 5,040,983 | 8/1991 | Binon . |
| 5,071,351 | 12/1991 | Green, Jr. et al. . |
| 5,073,111 | 12/1991 | Daftary .................................. 433/173 |
| 5,100,323 | 3/1992 | Friedman et al. . |
| 5,104,318 | 4/1992 | Piche et al. . |
| 5,122,059 | 6/1992 | Durr et al. . |
| 5,125,841 | 6/1992 | Carlsson et al. . |
| 5,135,395 | 8/1992 | Marlin .................................. 433/174 |
| 5,145,371 | 9/1992 | Jorneus . |
| 5,145,372 | 9/1992 | Daftary et al. ........................ 433/173 |
| 5,154,612 | 10/1992 | Carlsson et al. . |
| 5,188,800 | 2/1993 | Green, Jr. et al. . |
| 5,195,892 | 3/1993 | Gersberg . |
| 5,205,745 | 4/1993 | Kamiya et al. ........................ 433/173 |
| 5,209,659 | 5/1993 | Friedman et al. . |
| 5,209,666 | 5/1993 | Balfour et al. . |
| 5,213,502 | 5/1993 | Daftary .................................. 433/172 |
| 5,246,370 | 9/1993 | Coatoam . |
| 5,281,140 | 1/1994 | Niznick . |
| 5,286,195 | 2/1994 | Clostermann . |
| 5,292,252 | 3/1994 | Nickerson et al. . |
| 5,297,963 | 3/1994 | Daftary .................................. 433/172 |
| 5,316,476 | 5/1994 | Krauser . |
| 5,334,024 | 8/1994 | Niznick . |
| 5,336,090 | 8/1994 | Wilson, Jr. et al. . |
| 5,338,196 | 8/1994 | Beaty et al. . |
| 5,344,457 | 9/1994 | Pilliar et al. . |
| 5,362,234 | 11/1994 | Salazar et al. . |
| 5,362,235 | 11/1994 | Daftary .................................. 433/172 |
| 5,368,483 | 11/1994 | Sutter et al. .......................... 433/173 |
| 5,417,570 | 5/1995 | Zuest et al. . |
| 5,419,702 | 5/1995 | Beaty et al. . |
| 5,431,567 | 7/1995 | Daftary .................................. 433/172 |
| 5,433,606 | 7/1995 | Niznick et al. . |
| 5,437,551 | 8/1995 | Chalifoux . |
| 5,458,488 | 10/1995 | Chalifoux . |
| 5,476,382 | 12/1995 | Daftary . |
| 5,476,383 | 12/1995 | Beaty et al. . |
| 5,492,471 | 2/1996 | Singer .................................... 433/172 |
| 5,503,558 | 4/1996 | Clokie .................................... 433/173 |
| 5,533,898 | 7/1996 | Mena . |
| 5,538,426 | 7/1996 | Harding et al. . |
| 5,547,377 | 8/1996 | Daftary . |
| 5,564,921 | 10/1996 | Marlin .................................... 433/172 |
| 5,564,924 | 10/1996 | Kwan ...................................... 433/173 |
| 5,588,838 | 12/1996 | Hansson et al. . |
| 5,651,675 | 7/1997 | Singer . |
| 5,662,476 | 9/1997 | Ingber et al. .......................... 433/213 |
| 5,674,069 | 10/1997 | Osorio . |
| 5,674,071 | 10/1997 | Beaty et al. . |
| 5,674,073 | 10/1997 | Ingber et al. .......................... 433/213 |

OTHER PUBLICATIONS

"EsthetiCone™ system Components," Product Catalog, Prosthetics 1991.

Adell et al., "A 15–year Study of Osseointegrated Implants in the Treatment of the Endentulous Jaw," *Int. J. Oral Surg.*, 1981, pp. 387–416.

DIA™ Dental Imaging Associates, Implamed—The Source, *The Anatomical Abutment System*, Copyright Date Oct. 1991 on p. 10 (front cover, pp. 1–10, and back cover).

George Perri, DDS et al., *Single Tooth Implants, CDA Journal*, vol. 17, No. 3, Mar. 1989.

S.G. Lewis et al., *Single Tooth Implant Supported Restorations, Intnatl. Jrnl. of Oral & Maxillofacial Implants*, vol. 3, No. 1, pp. 25–30, 1988.

S.G. Lewis et al., *The "UCLA " Abutment, Intnatl. Jrnl. of Oral & Maxillofacial Implants*, vol. 3, No. 3, pp. 183–189, 1988.

Lazzara, Managing the Soft Tissue Margin: The Key To Implant Aesthetics, Practical Periodontics and Aesthetic Dentistry, vol. 5, No. 5, Jun./Jul. 1993 (8 pages).

Steri–Oss Dental Implants, "New Bio–Esthetic Technique Manual," (Oct. 1995) (6 pages).

Steri–Oss Dental Implants, "Osstium," an international publication (Fall 1995) (8 pages).

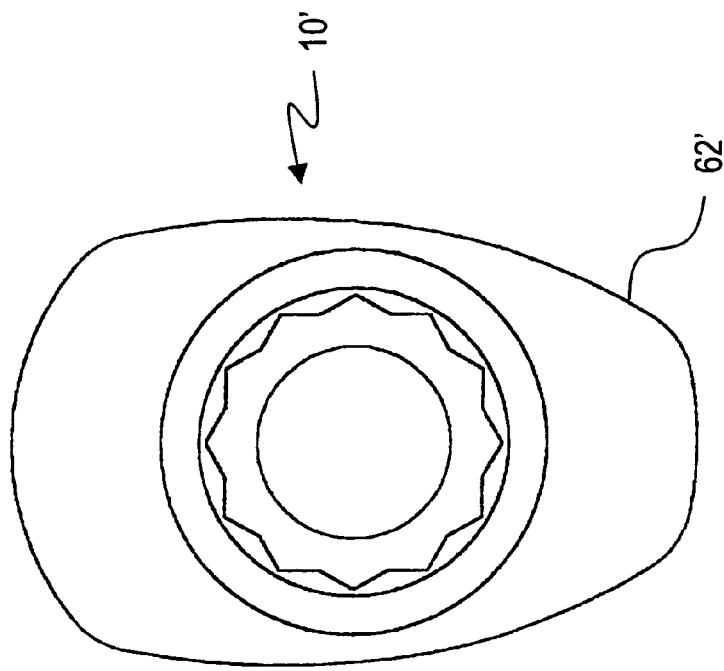
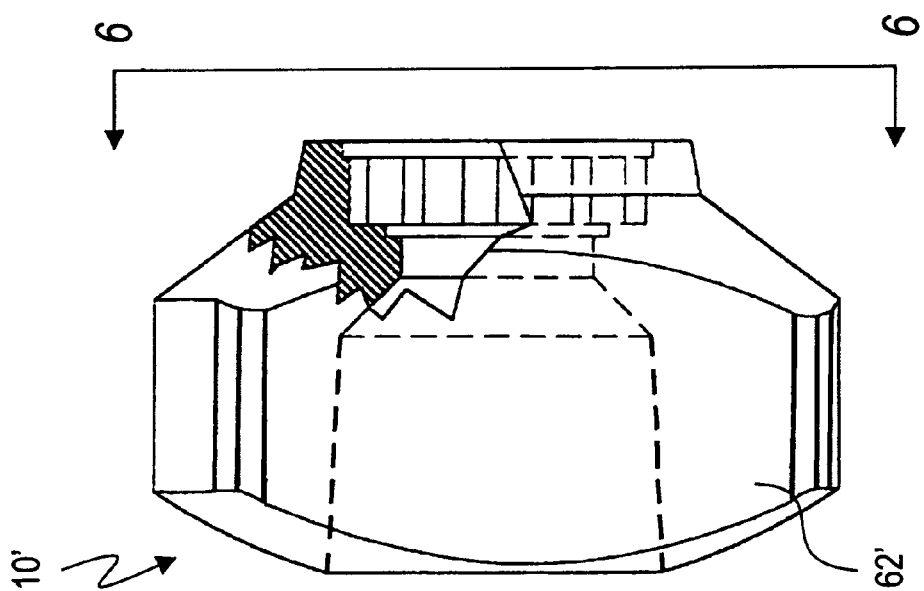

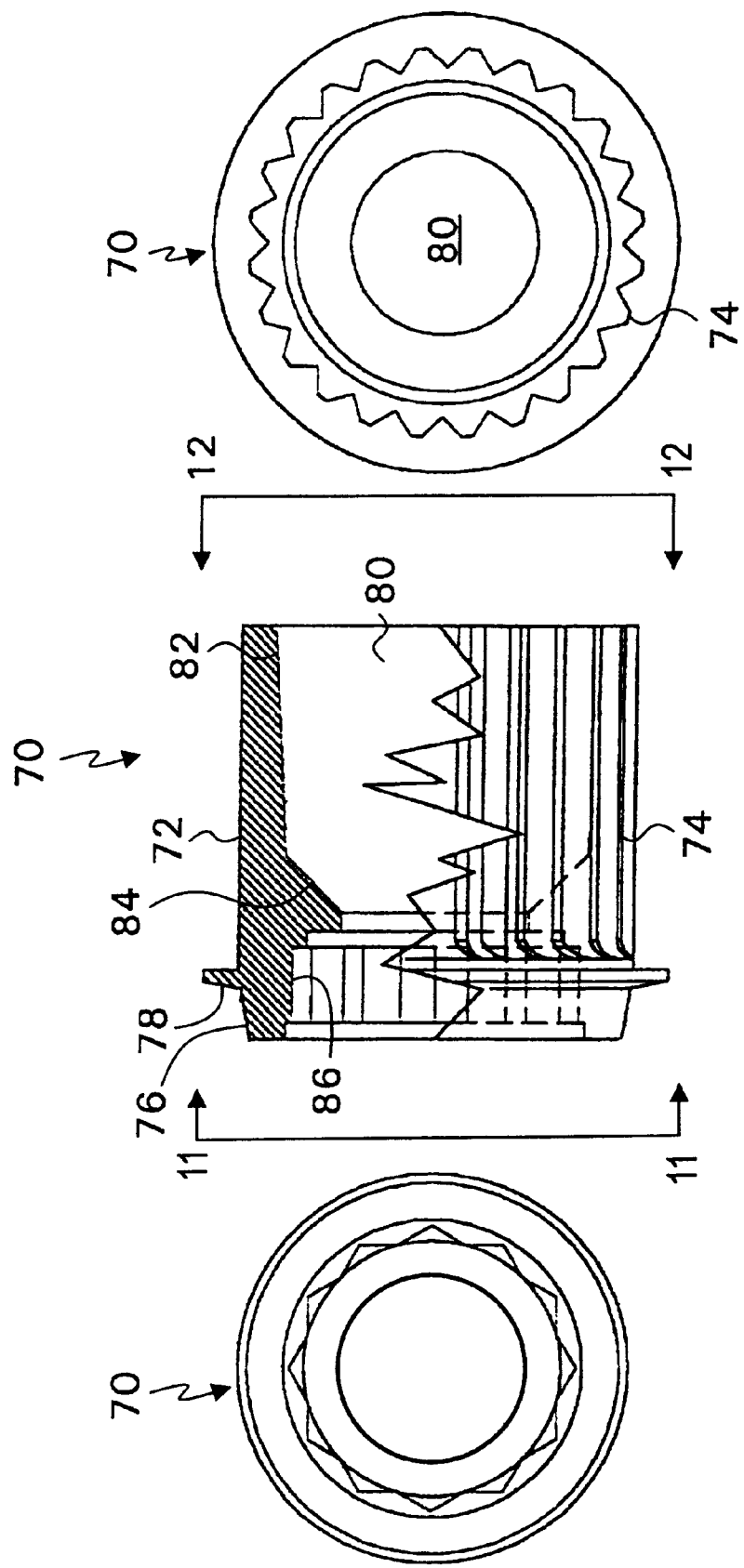

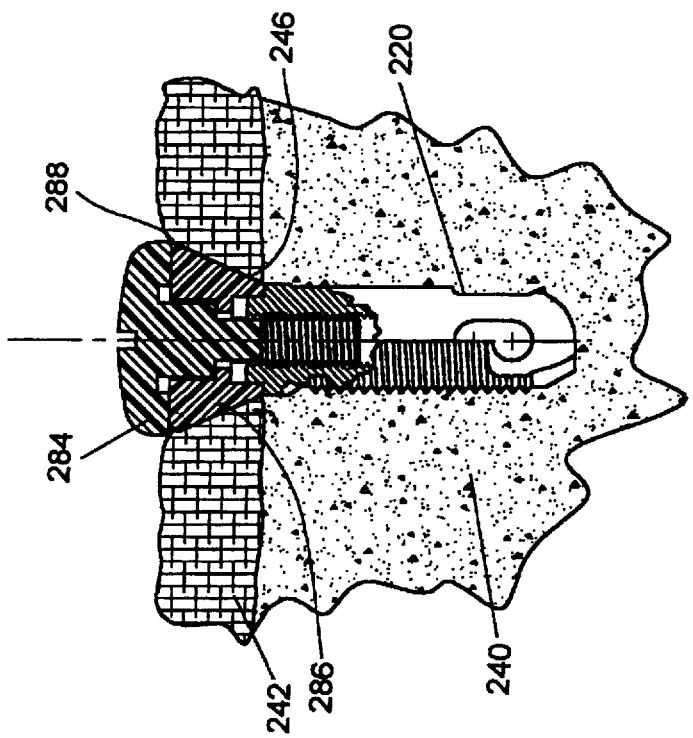
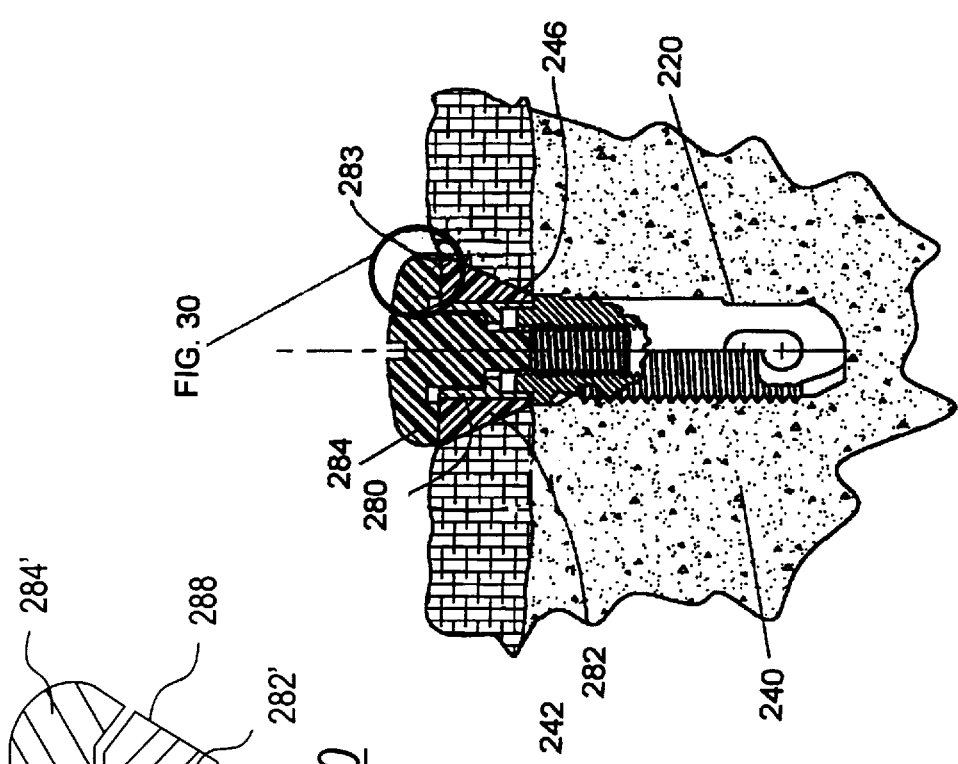
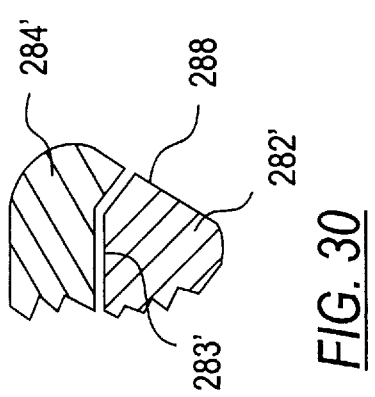

EMERGENCE PROFILE SYSTEM HAVING A COMBINED HEALING ABUTMENT AND IMPRESSION COPING

CROSS REFERENCES TO RELATED APPLICATIONS

This application is a continuation of U.S. Ser. No. 08/789,413, filed Jan. 29, 1997, now U.S. Pat. No. 5,873,722. This is a complete application claiming the benefit of copending Provisional Patent Applications Ser. No. 60/010,603, Filed Feb. 2, 1996, and Ser. No. 60/026,859, Filed Sep. 30, 1996.

FIELD OF THE INVENTION

This invention relates to improvements in dental restoration systems of the type which seek to mimic the natural anatomy of teeth being restored or replaced including, in particular, the size, shape and contour of the tooth where it emerges from the gum tissue. Furthermore, the present invention relates to methods and means to facilitate the work of dental practitioners seeking to achieve these results on root structures including artificial roots in the form of dental implants and the like.

BACKGROUND OF THE INVENTION

The dental restoration of a partially or wholly edentulous patient with artificial dentition is typically done in two stages. In the first stage, an artificial tooth root, usually an implant, is placed in the jawbone where it integrates with the jawbone. The gum tissue overlying the implant is generally sutured during this first stage. The gum tissue heals as the osseointegration process occurs.

Once the osseointegration process is complete, the second stage is encountered. In the second stage, the gum tissue is opened again so that the end of the dental implant is exposed. A component is then fastened to the exposed end of the dental implant to allow the gum tissue to heal therearound. Often, the gum tissue is healed such that the aperture that remains approximates the size and contour of the aperture that existed around the natural tooth that is being replaced. To accomplish this, the healing component attached to the exposed end of the dental implant must have approximately the same contour as the gingival aspect of the natural tooth being replaced.

Also during the second stage and while the healing component is removed, an impression coping is fitted onto the exposed end of the implant to take an impression of the region of the patient's mouth so that an artificial tooth can be fabricated in a laboratory with accuracy. Thus, the healing component and the impression coping are two separate components. Preferably, the impression coping has the same gingival dimensions as the healing component so that there is no gap between the impression coping and the wall of the gum tissue defining the aperture. If a gap exists, the impression material may fill the gap or the gingiva may tend to collapse into the gap. Consequently, a less than accurate impression of the condition of the patient's mouth is taken.

Because of the size of these mechanical components, the use of dental implants as artificial tooth roots for patients who are partially or wholly edentulous requires highly developed skills of manual dexterity over and above the medical and dental skills that are taken for granted in a dental practitioner. These mechanical parts, which are approaching the size of typical watch components, must be manipulated and fastened together inside a human mouth. Accordingly, there is a continuing search for improvements in the mechanical parts and the methods of using them to make it easier and less expensive for the dental practitioner to achieve both good mechanical results and good aesthetic results.

SUMMARY OF THE INVENTION

In its simplest form, the invention provides a set of anatomically shaped healing abutments to be used after the first stage of healing during which the dental implant osseointegrates with the bone tissue. During this second-stage process, each healing abutment in the set is sized and shaped to provide in the gingiva overlying a submerged implant an opening of a particular shape and size. Individual healing abutments may correspond, for example, to a molar, a premolar, or an incisor.

Sets of healing abutments may include three, four or more individual healing abutments. Regardless of the number of members of a set, all members have certain structural features in common. For example, a non-rotational attachment structure for mating each member with the same implant is one common feature. The size and shape of a passage through the abutment which receives a screw or bolt that attaches the abutment to the implant is another common feature. In accordance with one preferred embodiment of the present invention, that passage includes an entrance portion in the shape of a Morse taper for cooperating with a complementary surface on an impression coping part that is used to take an impression of the site after the attaching screw or bolt is removed during a later surgical stage. The passage also includes a conical seat portion to engage the attaching screw or bolt. Thus, the healing abutments of the invention are useful initially as healing abutments, and later as a component of a transfer coping assembly with which to make a model of the site in the mouth of the patient.

The invention further provides a duplicate set of the healing abutments to replace the original healing abutment when it becomes a part of a transfer coping and is needed to make the model. Thus, the duplicate set of healing components preserves the opening through the gum tissue that was formed around the original healing abutment. Instead of the exact components being used, an inexpensive plastic keeper element may be used to maintain the contour of the opening in the gingiva while the prosthetic tooth is being made.

Furthermore, the tapered portion of the passage in the duplicate healing abutment can alternatively be used to receive, in place of an attaching screw, a post on which a temporary dentition is fabricated while the permanent dentition is being prepared from the model. Throughout the second-stage surgical process, the opening in the gum tissue overlying the implant is preserved in the desired size, shape and contour, with little or no need for surgical intervention. This conserves the time of the clinician and minimizes discomfort to the patient.

In another embodiment of the present invention where a component is used as both a healing abutment and an impression coping, a core abutment is attached to a dental implant fixed in a jawbone of a patient. An emergence-profiler element, which may be shaped to the emergence contours of a particular type of natural tooth—e.g., molar, premolar, bicuspid, incisor, etc., is fitted onto the abutment where it meets the implant and serves to force the gingiva overlying the jawbone surrounding the implant to heal with an opening having the shape of the emergence profiler element. Thus, an "emergence profile" opening is developed which gives access to the implant through the gingiva.

The core abutment is preferably made of a rigid material that can be made in precise dimensions, such as titanium or a ceramic, or a combination of both. The emergence-profiler element can be made of a low cost moldable or castable material, such as a plastics material (e.g., acrylic) that is acceptable for dental use. It may be disposable so that it can be used for one patient only. It may also be modifiable so as to be altered at the chair of the doctor installing it. It may be combustible so that it can take part in a metal-casting process used to form an artificial tooth having the same emergence-profile shape.

The emergence-profiler elements are preferably made short. They need not have occlusive surfaces, since their essential purpose is to form the above-mentioned "emergence-profile" opening in the gingiva. Preferably, the emergence-profiler element is fitted non-rotationally to the abutment.

Conforming to existing practice, the core abutment may be fastened to the implant with an abutment screw that is "standard" in the industry. According to the invention, when an impression is taken of the region in the mouth where the artificial tooth is to be installed, the abutment screw is removed which leaves the abutment with its emergence profiler element in place on the implant and in the shaped opening. A transfer-coping screw is then substituted for the abutment screw. The abutment and its emergence-profiler element are thereby converted into components of a transfer or impression coping without moving them relative to the position they occupied as components of the healing abutment. The resulting transfer coping may be used in commonly known ways for taking impressions and for making dental laboratory models of the patient's case. A duplicate emergence-profiler element, which may be supported on a duplicate core abutment or otherwise, as hereinafter disclosed, may be placed on the implant as a keeper to hold the opening in the gingiva.

The invention will be described in greater detail with reference to the accompanying drawing illustrating exemplary embodiments of the invention.

BRIEF DESCRIPTION OF THE DRAWINGS

FIG. 5 is a side view of another healing abutment according to the invention;

FIG. 6 is a bottom view of the healing abutment of FIG. 5 taken along line 6—6;

FIG. 10 is a side view of a core on which to fabricate dentition;

FIG. 11 is an end view taken on line 11—11 of FIG. 10;

FIG. 12 is an end view taken on line 12—12 of FIG. 10;

FIG. 29 is a longitudinal-section view of a profile keeper;

FIG. 30 illustrates the keeper element of FIG. 29 with a modified upper surface; and FIG. 31 is a longitudinal-section view of another profile keeper.

BRIEF DESCRIPTION OF THE DRAWINGS

Figure 1:
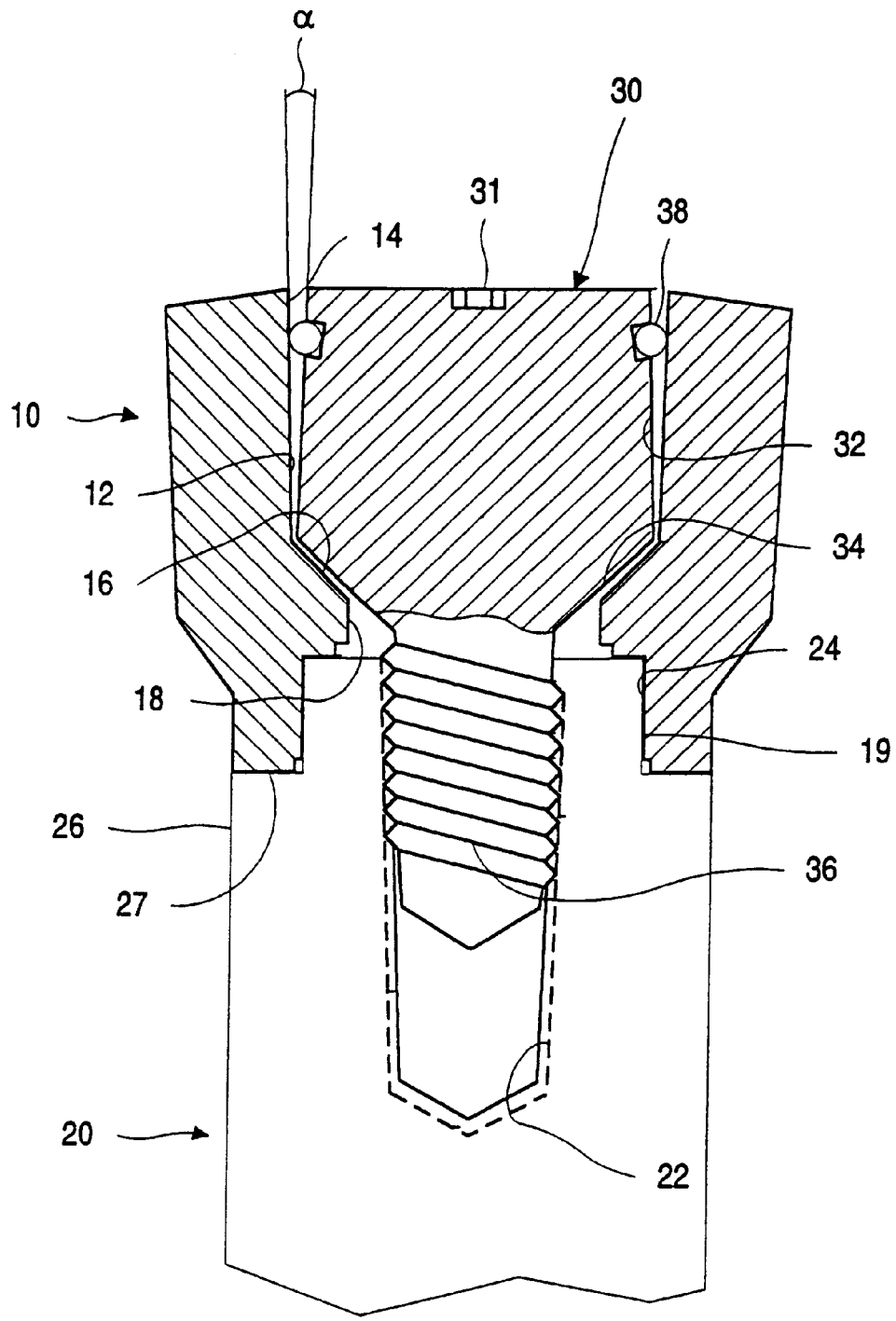
FIG. 1 is a longitudinal cross-sectional view of a healing abutment with an attaching screw.
Figure 2:
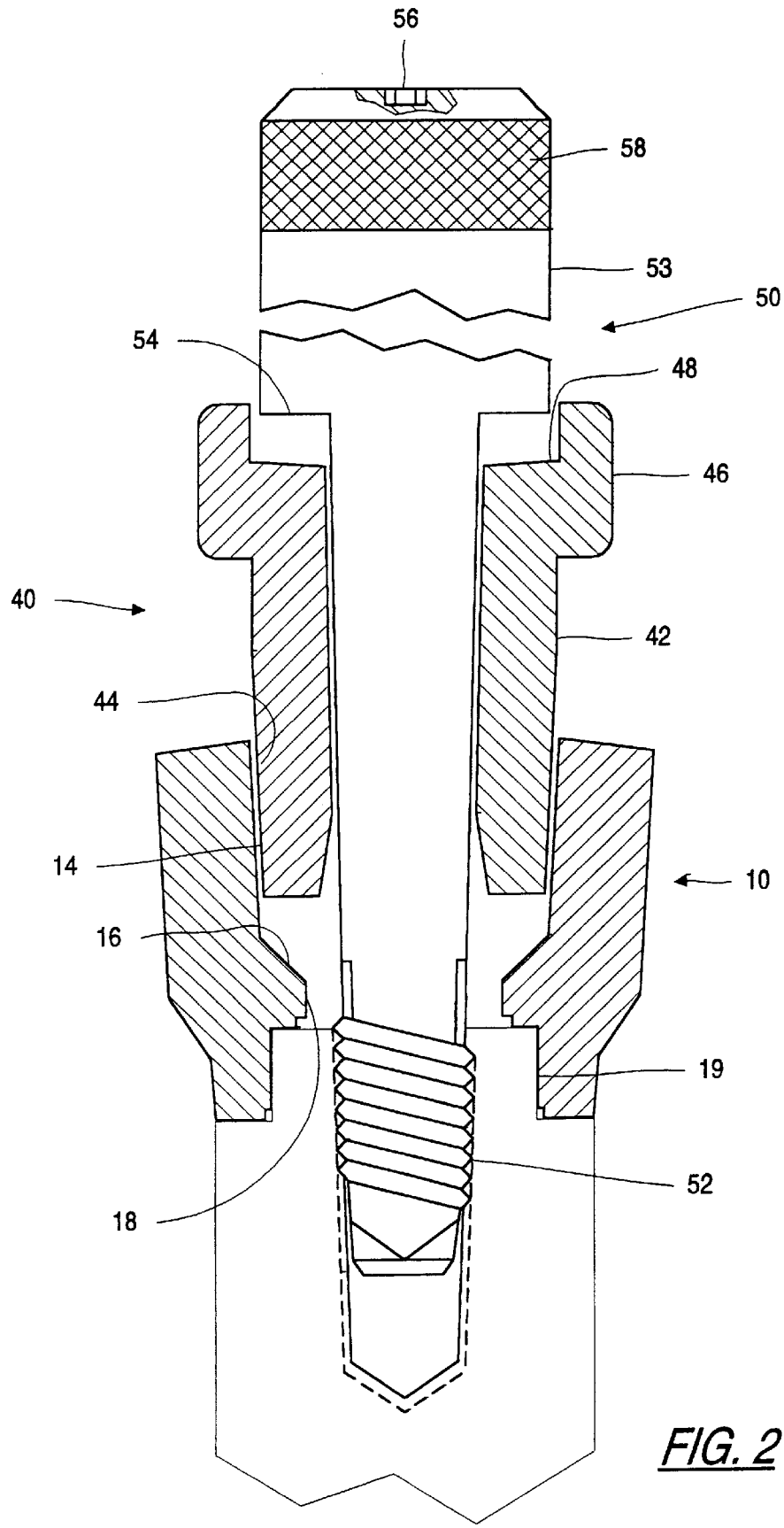
FIG. 2 is a longitudinal cross-sectional view of the healing abutment of FIG. 1 coupled to an impression coping part with a pick-up coping bolt in place.

The healing abutment 10 shown in FIGS. 1 and 2 has a through-passage 12 formed in a series of different sections 14, 16, 18 and 19. A first section 14, an entrance section, is a hollow cone dimensioned as a Morse taper with a taper angle α. Typically, taper angle α is in the range from about 1.0 degree to about 5.0 degrees and, preferably, is about 3.0 degrees. The second section 16, a seat section, tapers inward on an angle forming a surface for engaging a head of a bolt or screw. The angle of the seat section 16 is usually between 30 degrees and 60 degrees, and is preferably 45 degrees. The third section 18 has an internal diameter that is less than the diameter of the first and second sections 14 and 16 and a fourth section 19 positioned below it. The third section 18 is wide enough to permit the passage of a shaft of an attaching bolt 30 therethrough. The fourth section 19 includes structure which allows the healing abutment 10 to mate with an implant 20 as will be discussed in detail below with reference to FIGS. 3 and 4.

The implant 20, positioned below the healing abutment 10, includes a threaded bore 22 located along the axis of the implant 20. An orientation lock 24, generally in the shape of hexagon, is located at a gingival end 26 of the implant 20. Additionally, the gingival end 26 includes a flat surface 27, sometimes referred to as a table, against which mating components will abut.

The attaching bolt 30 has a generally cylindrical head portion 32 which fits within the entrance section 14 without engaging the Morse taper therein. A seating portion 34 of the bolt 30 engages the tapering seat section 16 of the healing abutment 10. A threaded shaft 36 engages the threaded bore 22 within the implant 20. The bolt 30 is used to fasten the abutment 10 to the implant 20 by tightening the threaded shaft 36 in the threaded bore 22 until the seating portion 34 of the bolt 30 becomes tight against the bolt-seat section 16 of the through-passage 12. Furthermore, the distance between the seating portion 34 and the upper edge of the bolt 30 is selected such that when the bolt 30 is in its tightened position, the upper surface of the bolt 30 is substantially flush with the upper surface of the healing abutment 10. An 0-ring 38 carried on the head 32 of the bolt 30 fills an annular gap left between the head 32 and the entrance section 14 near the outermost (widest) opening in the entrance section 14. A socket 31 on the exposed surface of the head portion 32 is shaped to accept a wrench (not shown) for turning the attaching bolt 30 into the implant 20. Because the fourth section 19 of the through-passage 12 encloses a companion orientation lock 24 of the implant 20, the abutment 10 can be locked against rotating around its longitudinal axis when being attached to the implant 20. Discussion of the exterior surfaces of the abutment 10 is reserved for the description of FIGS. 3, 4, 5 and 6.

In FIG. 2, the abutment 10 is shown appropriated for use as a part of a pick-up transfer coping 40 when mated with a coping head 42. The coping head 42, which is described in greater detail with reference to FIGS. 7 and 8, has a tapered end 44 which tapers at substantially the same angle as taper angle α (FIG. 1) of the entrance section 14 of the abutment 10. The coping head 42 is frictionally fastened to the abutment 10 through this Morse taper. The tapered end 44 of the coping head 42 does not touch the seat section 16 of the through-passage 12.

To convert the healing abutment 10 for use in a transfer-coping function, the attaching bolt 30 shown in FIG. 1 is removed. The coping head 42 is placed in the entrance section 14 and a coping bolt 50 (shown in detail in FIG. 9) is used to fasten the transfer coping 40 to the implant 20 through a threaded shaft 52 at the lower end of the coping bolt 50. A widened head section 46 of the coping head 42 has a recessed shoulder 48 on its remote upper surface. The coping bolt 50 has a widened head portion 53 with an annular surface 54 at its lower end for contacting the shoulder 48 when the threaded shaft 52 is tightened in the threaded bore 22 of the implant 10, thereby forcing the Morse-tapered entrance section 14 and the tapered end 44 together. The coping head 42 has a wrench socket 56 at its upper end and a knurled surface 58 on its side to facilitate this tightening.

Once the coping head 42 has been fastened to the abutment 10 by the bolt 50, the impression can be taken. Before removing the impression material, the bolt 50 is removed. Then, the impression material is pulled away from the site and with it comes the coping head 42 since it is encased well within the impression material. Additionally, the engagement of the coping head 42 and the abutment 10 at the tapered portion 44 and the entrance section 14, respectively, is enough to permit the coping head 42 and the abutment 10 to be retracted with the impression material at one time.

After the abutment 10 is removed, the clinician places a duplicate abutment into the opening vacated by the abutment 10 to preserve the contour in the opening of the gingiva leading to the implant 20. Alternatively, the opening can be maintained by an inexpensive keeper element that attaches to the implant and has the same size and contour of the abutment 10, but is made from a plastic material.

Figure 4:
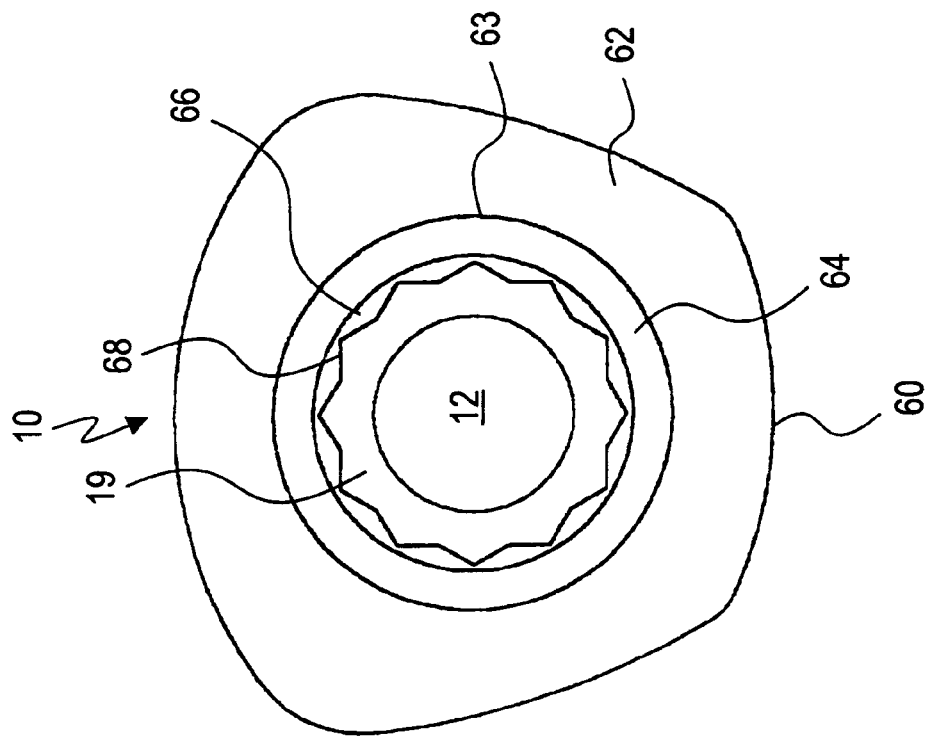
FIG. 4 is a bottom plan view of the healing abutment taken on line 4—4 in FIG. 3.
Figure 3:
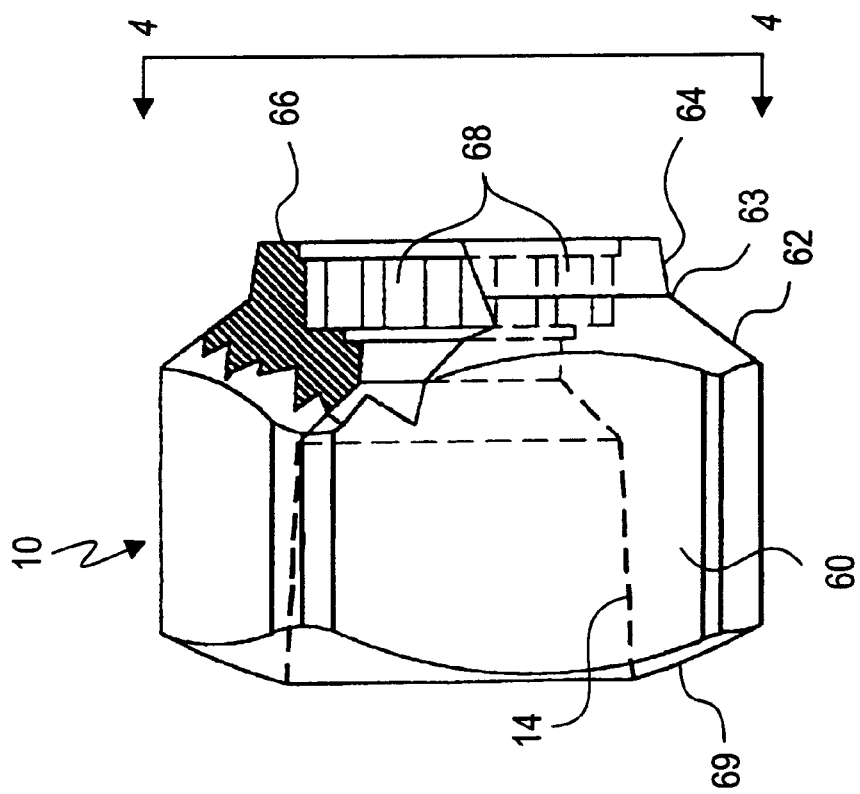
FIG. 3 is a side view of the healing abutment shown in FIG. 1.

FIGS. 3 and 4 illustrate the exterior features of the healing abutment 10 of FIG. 1. The healing abutment 10 has a main body with a cross-sectional shape and dimensions that are suitable for replicating the emergence profile of an incisor, as is shown most clearly in FIG. 4. The main body 60 is wider than the implant 20 (FIG. 1). A first tapered section 62 extends downwardly from the main body 60 of the abutment 10 and tapers from the non-round configuration of the main body 60 to a round configuration having a diameter at a boundary 63 that is larger than the implant 20. The boundary 63 separates the first tapered section 62 from a second tapered section 64. The second tapered section 64, which tapers on a smaller angle than the first tapered section 62, extends from this boundary 63 to a subgingival end 66 where the diameter is the same as the gingival end 26 of the implant 20 (FIG. 1). The second tapered section 64 tapers at an angle generally in the range from about 5 degrees to about 15 degrees, with 10 degrees being preferable. The second tapered section 64 is provided to distance the wider-flaring, first tapered section 62 from the gingival end 26 of the implant 20, if that is desired. The second tapered section 64 may be omitted, in which case the first tapered section 62 tapers directly to the diameter of the gingival end 26 of the implant 20. In another alternative embodiment, the first tapered section 62 may merge smoothly into the second tapered section 64, without the discrete boundary 63 between them. At a supragingival end 69, the main body 60 has a generally arcuately shaped surface.

The fourth section 19 of the through-passage 12 encloses the orientation lock 68 which is shown as a duo-hexagonal shaped socket suitable for providing on the hexagonal orientation lock 24 of the implant 20 twelve discrete, fixed, angular positions 30 degrees apart. This type of orientation lock 68, sometimes known as a twelve-pointed star, is in widespread use at the present time. Another suitable type of orientation lock is a simple hexagonal lock. Yet another type of orientation lock that is used when the implant has an internal hexagonal socket is one which includes a hexagonal projection that is inserted into such an internal hexagonal socket.

FIGS. 5 and 6 show another healing abutment 10' that is very similar to the abutment 10 of FIGS. 3 and 4 except that the main body 62' has a cross-sectional configuration with a more oval shape. This type of configuration is suitable for replicating the emergence profile of a tooth having smaller mesial-distal dimensions than a molar, such as a premolar. Furthermore, the sets of healing abutments may include members with configurations that replicate the natural emergence profile of each type of tooth. In a further embodiment, a set may include not only different configurations for replicating each tooth, but different sizes of each configuration may be included as well. For example, the set of healing components may include the members with the general configuration of the healing abutments 10 and 10' but with maximum dimensions of 5.0 mm, 5.5 mm, and 6.0 mm. The heights of each member may also be varied as well. In any event, the through-passage 12 of each member would be the same so that the same bolt 30 is used to attach any member of the set to the implant 20. Uniformity of the through-passage 12 also permits the use of the same transfer coping head 42 for each member.

Figures 7, 8:
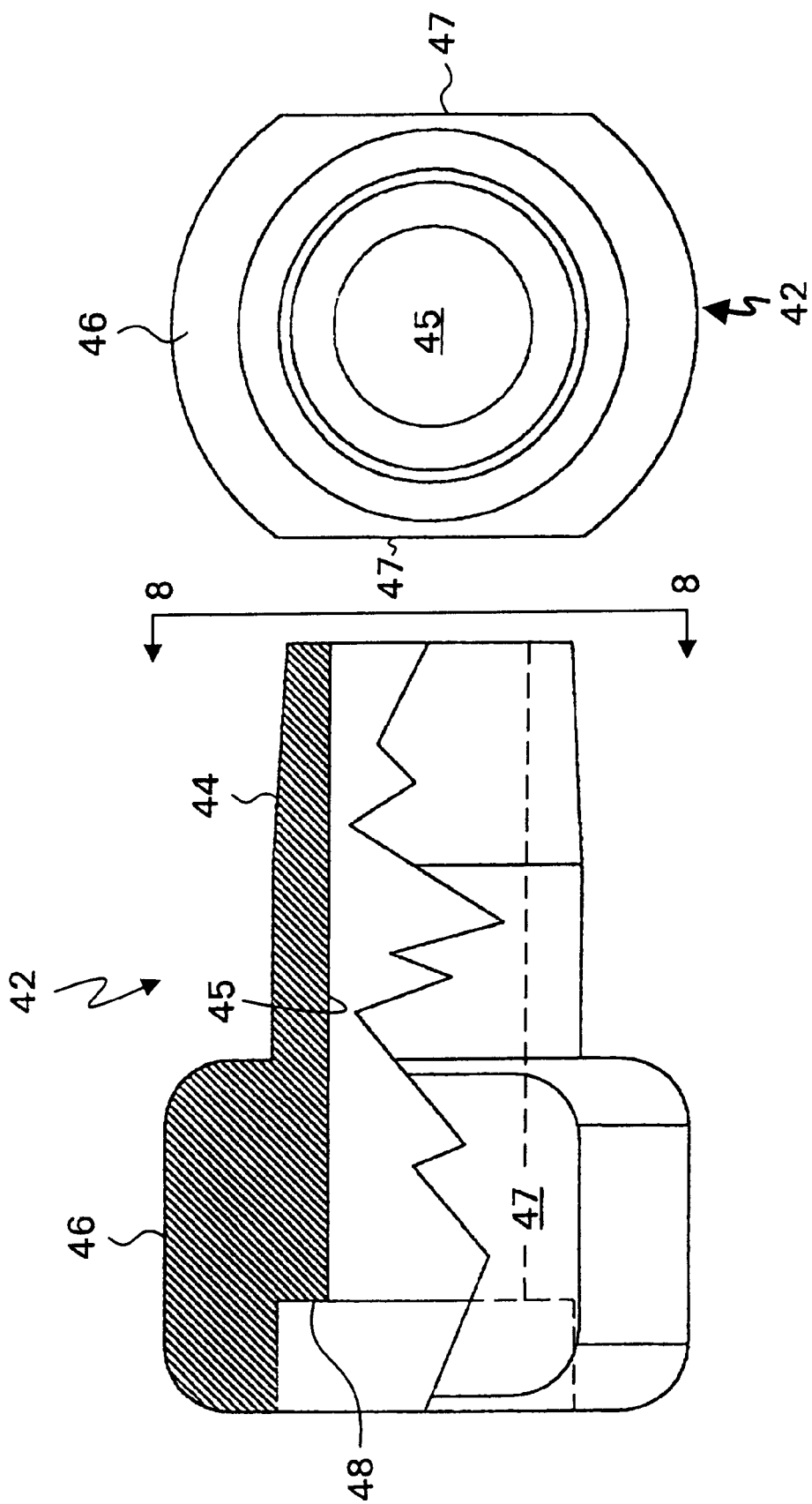
FIG. 7 is a side view of the transfer coping part of FIG. 2 partially broken away.
FIG. 8 is an end view taken along line 8—8 of FIG. 7.

The coping head 42 is shown in greater detail in FIGS. 7 and 8. The widened head section 46 has two parallel flat sides 47, as is seen in FIG. 8, to provide orientation memory in impression material that is placed around the coping head 42. The parallel flat sides 47 are exemplary only; another suitable memory-providing configuration may be substituted. For example, an array of circumferentially symmetrical impression interlocking elements may be placed around the coping head 42. Also, the slight taper of the tapered end 44 is also more readily seen in FIG. 7. A through-passage 45 is provided for the coping bolt 50, which is shown in detail in FIG. 9. The head of the coping bolt 50 engages the shoulder 48.

Figure 9:
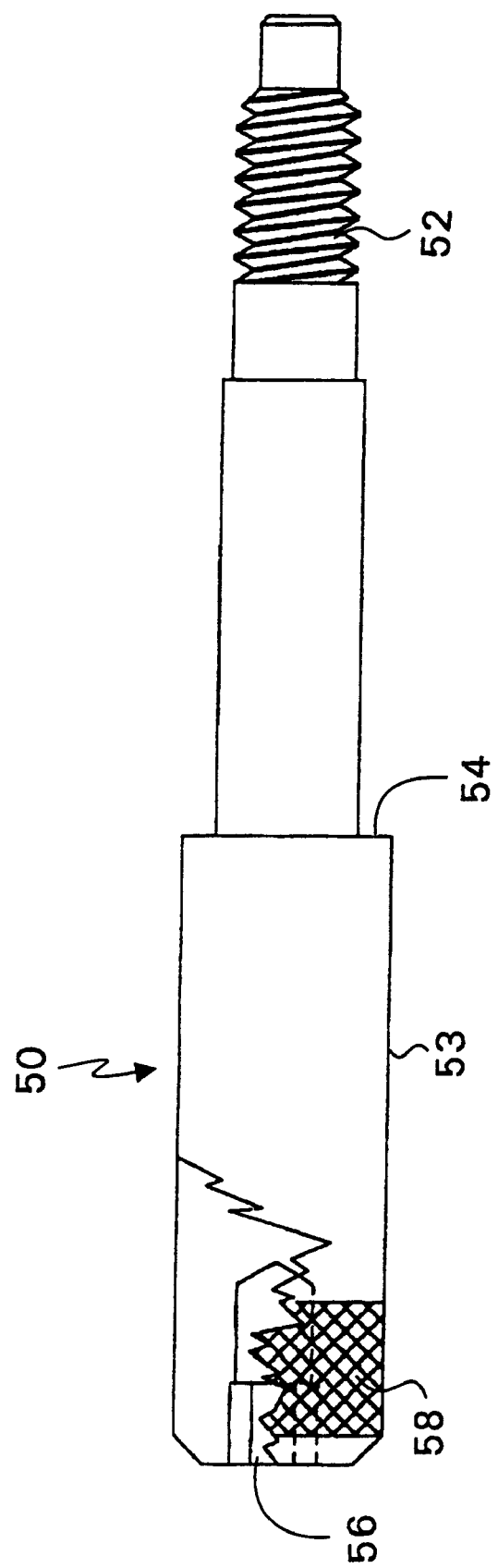
FIG. 9 is a side view of the pick-up coping bolt shown in FIG. 2.

In FIG. 9, the coping bolt 50 is shown, partially broken away, with its threaded shaft 52 at one end. The annular surface 54 engages the shoulder 48 of the coping head 42. The widened head portion 53 includes the wrench socket 56 and the knurled surface 58. The distance from the annular surface 54 to the upper surface adjacent to the wrench socket 56 is selected to provide the clinician with enough length such that the socket 56 is exposed through the impression material placed around the transfer coping 40.

FIGS. 10, 11 and 12 show a core 70 suitable to support an artificial tooth (not shown). The core 70 has a generally cylindrical outer shape with the outer surface 72 being covered with an array of axially extending splines 74. The subgingival end 76 tapers typically on an angle of about 10 degrees. A radially extending flange 78 is provided between the cylindrical surface 72 and the tapered surface of the subgingival end 76. Internally, the core 70 shares many features in common with the healing abutments 10 (FIGS. 1, 3–4) and 10' (FIGS. 5–6). These include a through-passage 80 having a Morse-tapered section 82, a seating section 84 and the orientation-lock section 86. Because the sections 82, 84, as the of the through passage 80 are dimensioned the same as the corresponding sections of the through passage 12 of the healing abutments, the attaching bolt 30 of FIG. 1 can be used to attach the core 70 to the implant 20.

The core 70 can support various types of materials which replicate a natural tooth. For example, an acrylic can be used on the core. This acrylic can be molded around the core. Alternatively, the clinician may possess a set of anatomically shaped healing members which are preformed. Each healing member would have a bore therethrough that has substantially the same size as the cylindrical surface 72 of the core 70. The clinician then chooses the correct member for the patient and slides it over the core 70. The splines 74 would assist in keeping the healing member on the core 70. Thus, the core 70 would be a modular component capable of being used with various shapes of healing members.

Figure 13:
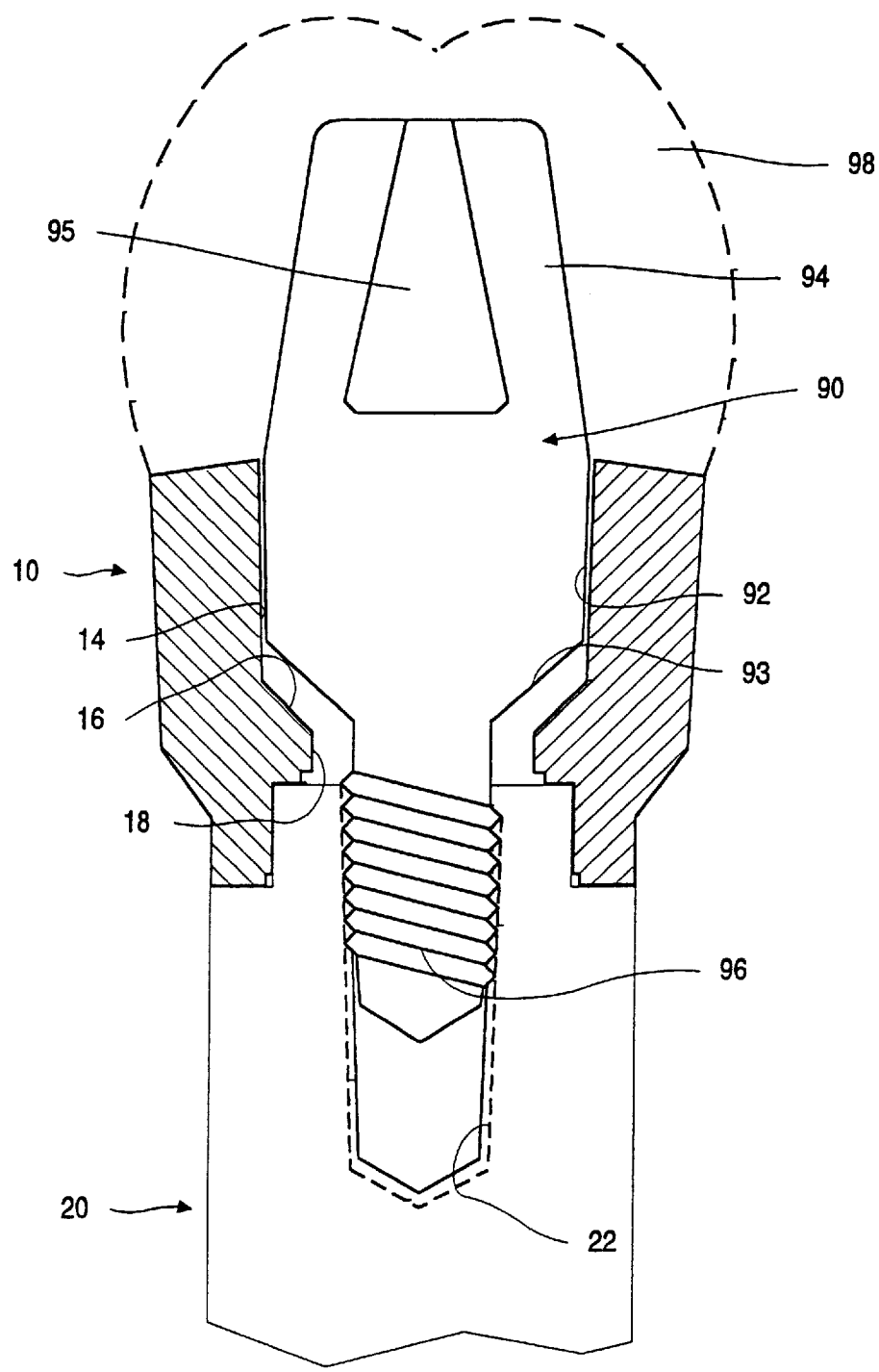
FIG. 13 is a side view, partly in section, of a post for a temporary crown supported by the healing abutment of FIG. 1.
Figure 17:
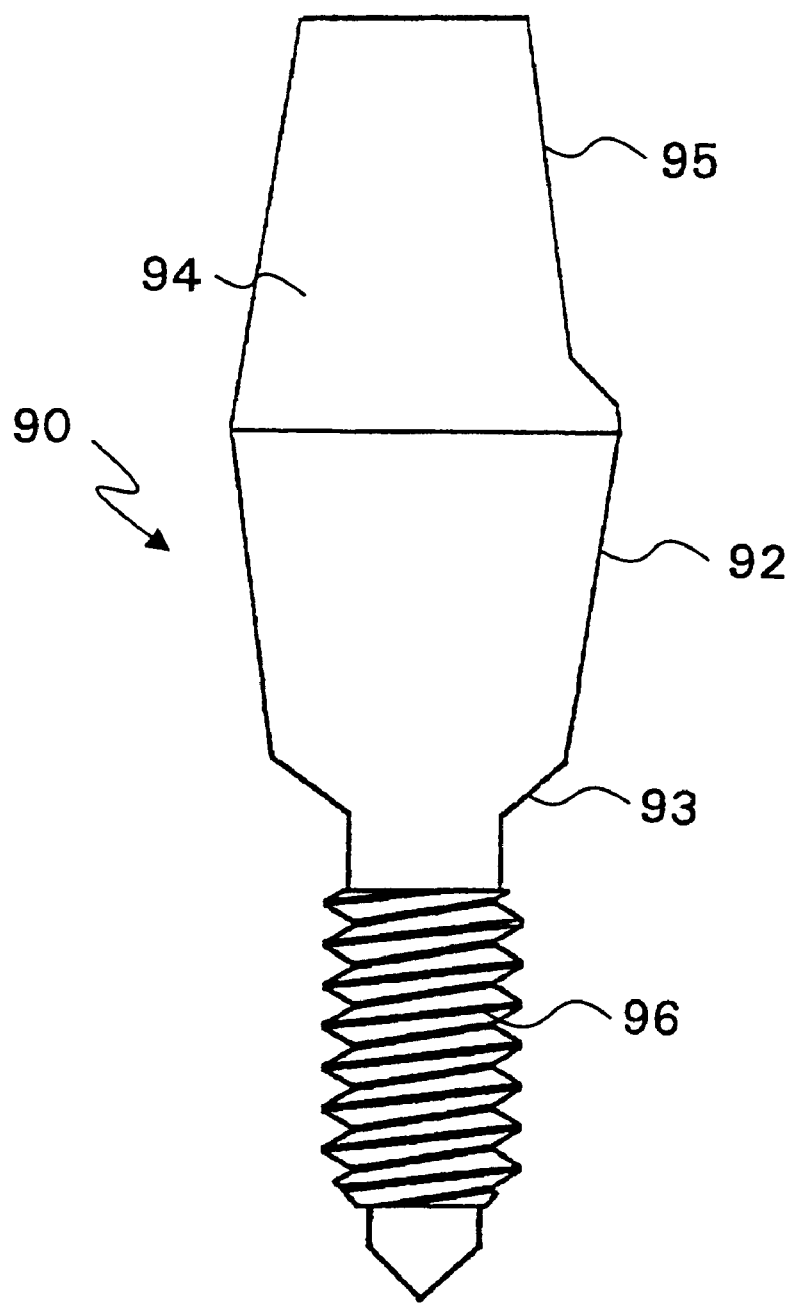
FIG. 17 shows another post useable in combination with a healing abutment of the invention.

FIG. 13 illustrates a crown-supporting post 90, described in detail in FIG. 17, which may be fixed to the healing abutment 10 in place of the bolt 30. Like the transfer coping head 42, the post 90 has a tapered end 92 having a taper which matches the Morse taper of the entrance section 14 of the abutment 10. An angled portion 93 of the post 90 resides above the seating section 16 of the abutment 10 so that there is no interference between the angled portion 93 and seating section 16 when the tapered end 92 engages the entrance section 14. A supragingival end 94 of the post 90 extends supragingivally from the abutment 10 and includes a flattened side 95. The post 90 includes an integral threaded shaft 96 extending downwardly from the tapered end 92 which engages the threaded bore 22 of the implant 20 to attach the post 90 and the abutment 10 to the implant 20. The supragingival end 94 of the post 90 supports a crown 98 that is shown in dashed-lines. The illustrated combination of the post 90 and the abutment 10 is preferably suitable for temporary dentition. A temporary crown may be made of dental acrylic, for example. By using acrylic, the clinician can fashion the temporary dentition at chair-side to the precise size and shape needed by the patient.

Figure 14:
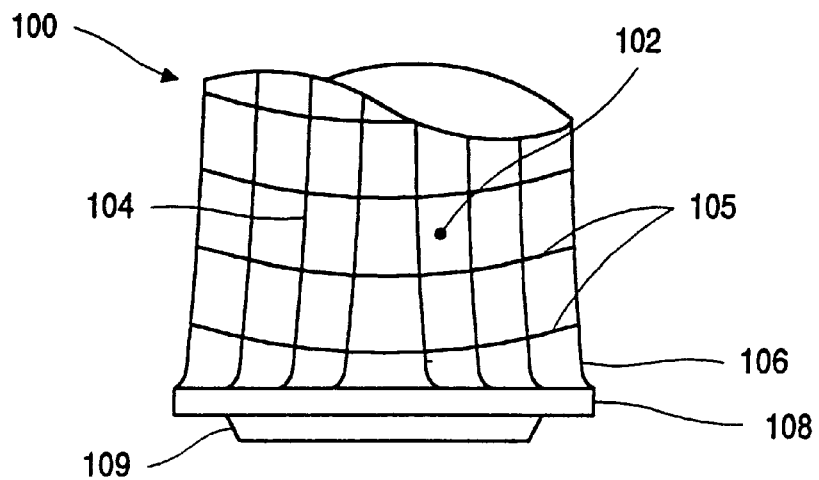
FIG. 14 is a side view of a core similar to the core of FIGS. 10—12 modified to retain temporary dentition.

FIG. 14 illustrates a core 100 similar to the core 70 of FIGS. 10–12. Core 100 has an outer surface 102 that includes not only axially extending splines 104, but also circumferential splines 105 to improve the ability of the core 100 to retain acrylic crown material. Alternatively, the outer surface 102 of the core 100 may be knurled for acrylic retention. The outer surface 102 of the core 70 also has a flared region 106 near its lower where the outer surface 102 transitions into platform 108. Below the platform 108, a subgingival end 109 tapers inwardly at an angle of about 10 degrees. The interior structure of the core 100 is the same as core 70 such that the core 100 includes a bore with an entrance section having a Morse taper, a seat section, and a lower section that has the structure to interlock with the fitting at the top of the implant.

Figure 15:
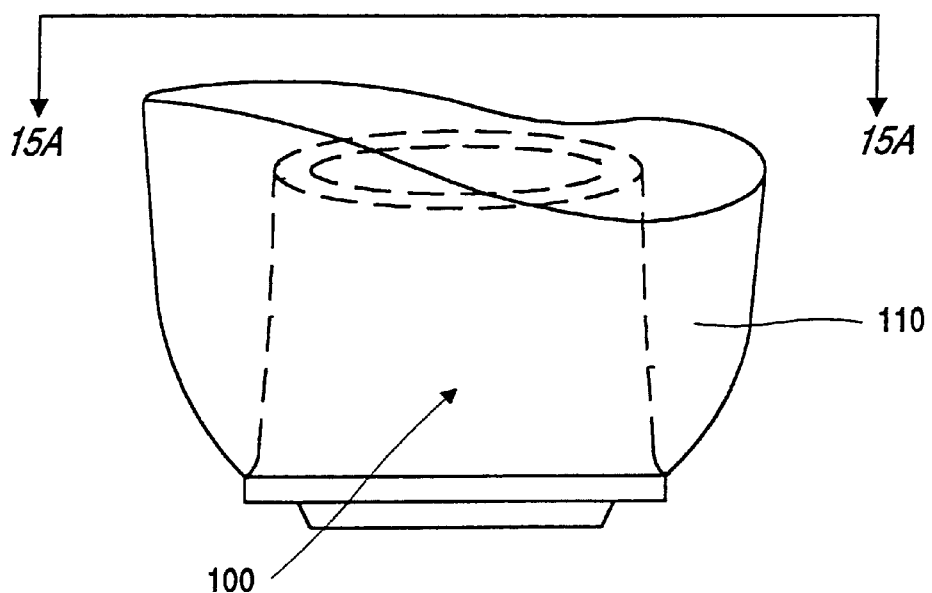
FIG. 15 shows the core of FIG. 14 combined with a covering of temporary tooth material.
Figure 15A:
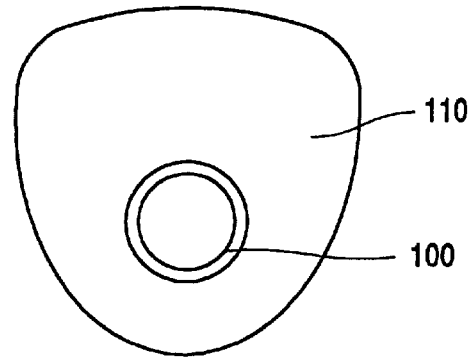
FIG. 15A is a top view of FIG. 15 taken on line 15A.

The cores 70 and 100 may be furnished to the dental practitioner as a separate item as core 70 is shown in FIGS. 10, 11 and 12, or as core 100 is shown in FIG. 14. Alternatively, a combination of the core 100 with a body 110 of crown material such as acrylic attached to it, as is shown in FIG. 15, may be furnished. Desirably, the attached body of crown material may have an anatomical shape for use as a healing abutment, as is shown in FIG. 15A. If an anatomical shape is furnished, the clinician can modify it at chair-side. Whether or not the body of crown material is furnished with an anatomical shape, the clinician can fashion a desired shape to suit the individual patient. However, less modification of the body of the tooth is needed if an anatomical shape is employed.

Figure 16:
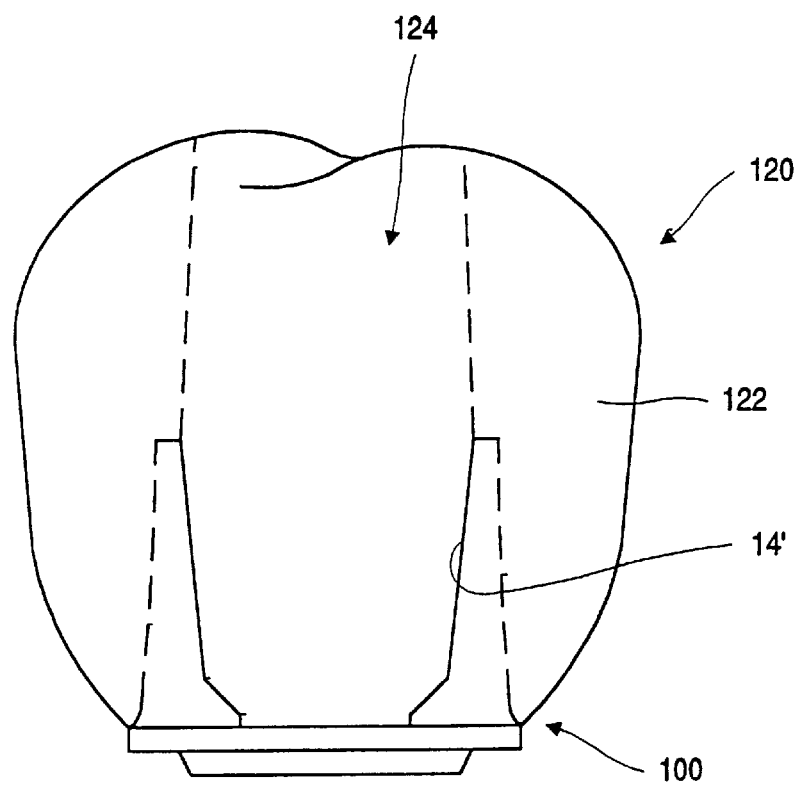
FIG. 16 shows the core of FIG. 14 combined with a pre-formed crown.

In like manner, the core 100 can be furnished in combination with a body 120 of crown material 122 in the shape of a tooth, as is shown in FIG. 16. Here, the tooth material 122 has a through-bore 124 sized to approximately the same diameter as the opening into an entrance section 14' of the core 100 having the Morse taper. Thus, it is large enough for the passage of an attaching bolt like the bolt 30 shown in FIG. 1 so as to attach the combination of the core 100 and the body 120 to an implant such as the implant 20 in FIGS. 1–2. The through-bore 124 is closed after being installed via the use of common techniques. Alternatively, the body 120 may be furnished without a specific tooth shape, leaving to the clinician the task of custom-preparing a tooth for an individual patient.

In FIG. 17, the post 90 from FIG. 13 is illustrated in detail. The tapered portion 92 is more readily seen as is the contour of the angled portion 93. The supragingival end 94 extends from the tapered portion 92 and includes the flattened side 95 that prevents the rotation of any material placed around it such as the crown material 98 (FIG. 13) or impression material if an impression is to be taken. The impressions that could be taken by post 90 would require the post 90 to be registered on the abutment and then removed from the implant. The registering may be as simple as a mark on each component. After the abutment is removed, the post is then re-registered with the abutment on an implant analog over which the impression material would then be placed. The flattened side 95 on the supragingival end 94 can also be used to facilitate turning the post 90 into the abutment and turning its screw into the implant bore 22. As will be appreciated, the surfaces of the supragingival end 94 of the post 90 can be roughened or otherwise treated to retain dental crown material, as is described with reference to FIGS. 13 and 18. Although the post 90 has been shown with an integral threaded shaft 96, the post 90 could be designed with an internal bore that receives a bolt (like bolt 50 shown in FIG. 9) to attach the post to the implant.

Figure 18:
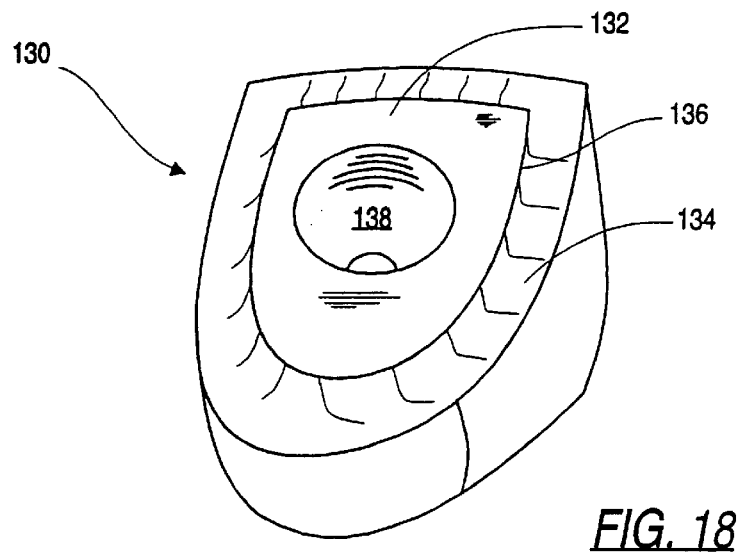
FIG. 18 is an isometric view of an alternative abutment.

FIGS. 18–21 illustrate an embodiment of the invention that is useful for a cementable tooth restoration and, preferably, a permanent tooth restoration. FIG. 18 illustrates an alternative healing abutment 130 that has a generally flat top surface 132 at its gingival end and a chamfer 134 around the periphery of the top surface 132. The top surface 132 and the chamfer 134 meet at a curved transition region 136. Alternatively, the transition region 136 could be planar such that only defined corners exist between the top surface 132 and the chamfer 134. In all other respects the abutment 130 of FIG. 18 is similar to healing abutments 10 (FIGS. 3 & 4) and 10' (FIGS. 5 & 6) of the present invention. That is to say that the healing abutment 130 has a through-passage 138 with all of the same elements as the through-passage of the previously mentioned healing abutments 10 and 10'.

Figure 19:
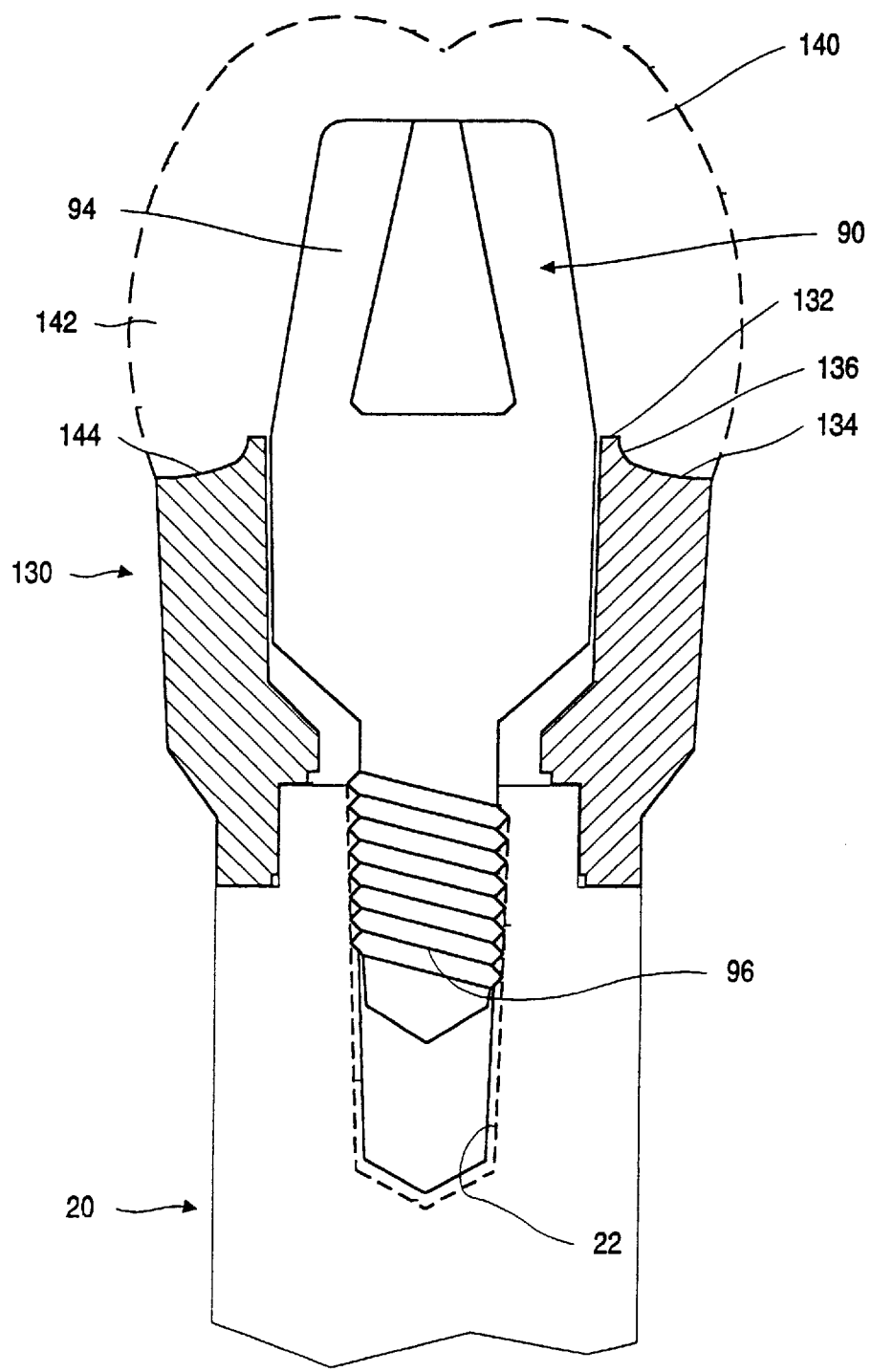
FIG. 19 is a side-sectional view of a cementable restoration using the alternative abutment of FIG. 18.

In FIG. 19, the abutment 130 of FIG. 18 is attached to the implant 20 through the post 90 of FIG. 17. A crown 140, shown in dashed-lines, is fixed to the supragingival end 94 of the post 90, as by cementing. At its gingival end 142, the crown 140 has an extending rim 144 which fits into the depression of the chamfer 134 of the abutment 130 to form a tight margin with the abutment 130. Thus, the geometry of the abutment 130 facilitates a tighter bond between the abutment 130 and the crown 140.

Figure 20:
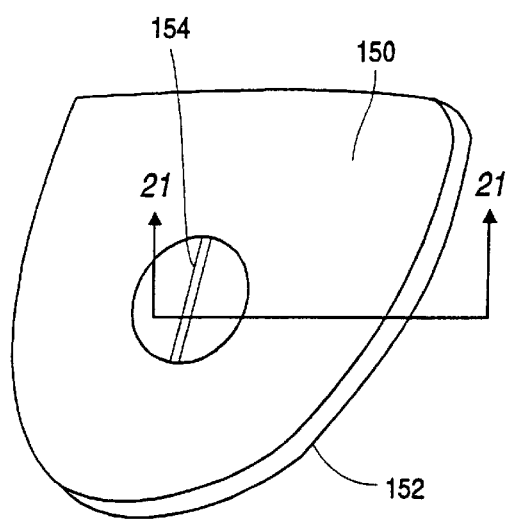
FIG. 20 shows a healing cap for the alternative abutment of FIG. 18.
Figure 21:
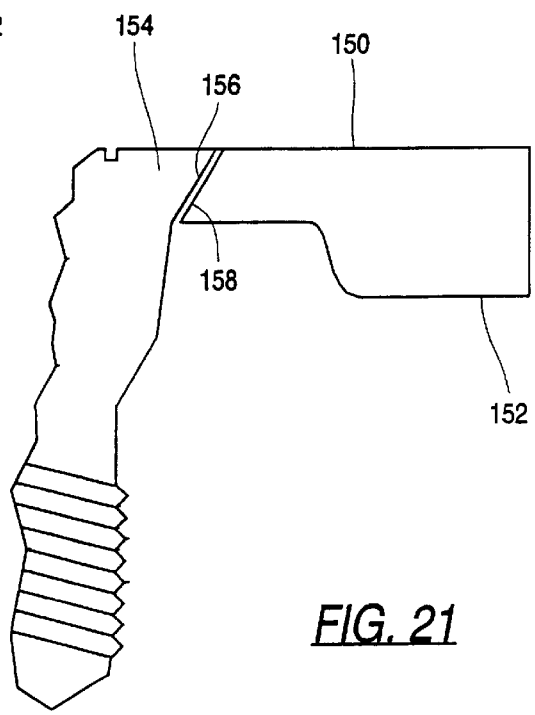
FIG. 21 is a partial section on line 21—21 in FIG. 20 showing the mating of the healing cap and the alternative abutment.

FIGS. 20 and 21 illustrate a cover 150 which is useful to close the entrance section of the through-passage 138 of the abutment 130 so that abutment 130 can function as a healing member. The cover 150, which can be made of any desired material including a plastic material, is held onto the abutment 130 by a bolt 154 that is similar to bolt 30 (FIG. 1) except it has an angled surface 156 to engage a corresponding angled surface 158 of the cover 150. As is shown in FIG. 21, this cover 150 has an extending rim 152 with a shape corresponding to the shape as the chamfer 134 and the transition region 136. The rim 152 also has a shape of the extending rim 144 of the crown 140 in FIG. 19. Once the cover 150 fits onto the abutment 130, the combination of the cover 150 and the abutment 130 serves as a healing member with a flat upper surface. Alternatively, if the flat surface 132 of the abutment 130 is not substantially above the chamfer 134, then it may be possible to use the bolt 30 of FIG. 1 to close the through-passage 138 such that no cover 150 is needed and the abutment 130 is a healing member with an uneven upper surface.

Figure 22:
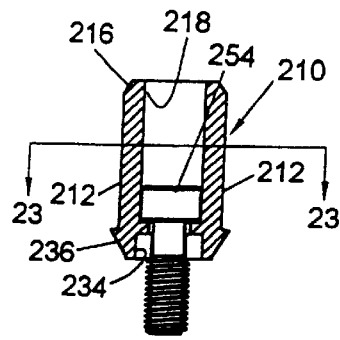
FIG. 22 is a longitudinal section through a core abutment of an alternative embodiment of the present invention.
Figure 23:
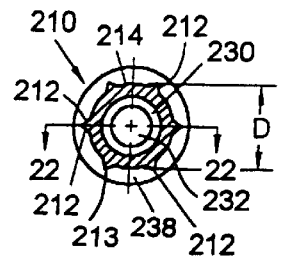
FIG. 23 is a transverse section through line 23—23 in FIG. 22.
Figure 25:
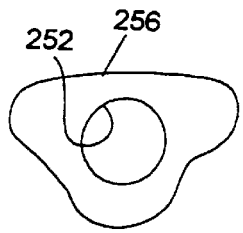
FIG. 25 is a top view of another emergence-profiler component.
Figure 26:
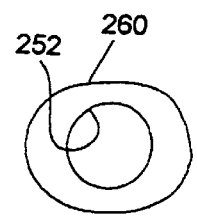
FIG. 26 is a top view of still another emergence-profiler component.
Figure 27:
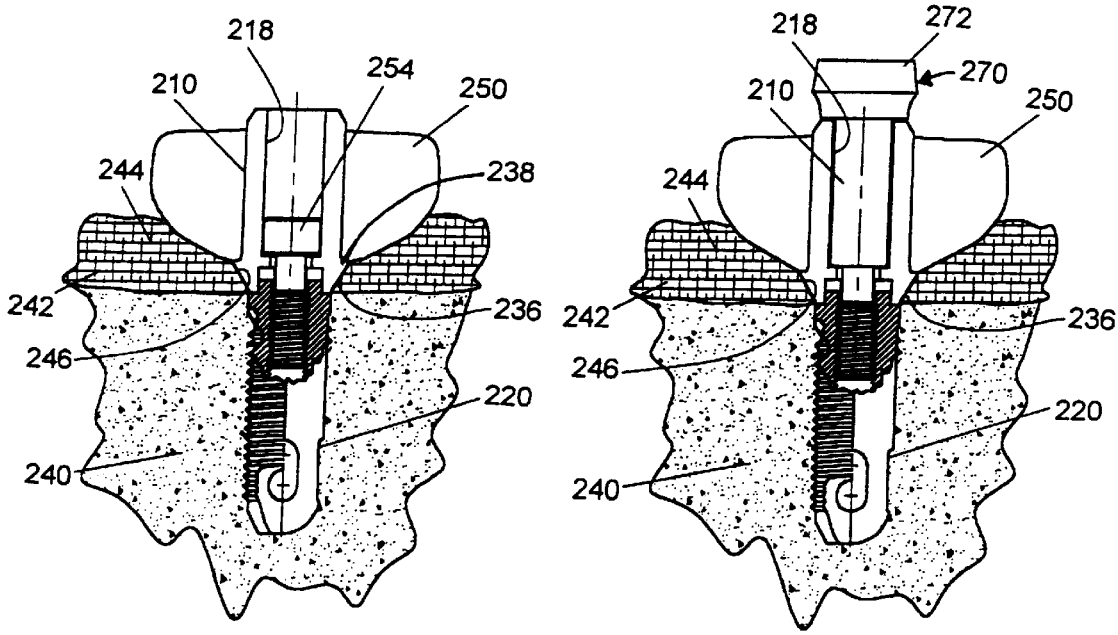
FIG. 27 is a side view of the healing abutment of FIG. 26 on the core abutment which is mounted on a dental implant.

FIGS. 22–28 illustrate an alternative embodiment of the present invention in which the healing component can also be used as an impression coping. Referring first to FIGS. 22, 23 and 27, a core component 210 is generally tubular in form with an outer diameter "D" substantially the same as the diameter of the implant 220 (FIG. 27) on which it is to be mounted. Longitudinally-oriented ribs 212 are on the outer surface 214 which defines the diameter "D". Preferably, the ribs 212 have sharp edges 213, seen in FIG. 23. The ends 16 of the ribs 212 at the supragingival end 218 of the core component 210 slope toward the sharp edges 213. Six ribs 212 are illustrated in FIG. 23, but the number of ribs can be different.

In other structural respects that are illustrated in the drawings, the core components 210 may be similar to known abutments. The transverse member 230 which defines a screw hole 232 and a top surface of a socket 234 is a known feature on existing abutments. The expanded subgingival end 236 with its shoulder 238 is also known.

In FIG. 27, the core component 210 is shown installed on a dental implant 220 which is fixed in bone 240 having overlying gingiva 242 with an aperture 246 giving access to the implant 220. As is the prevailing dental practice, the implant 220 is substantially entirely encased in the bone 240. The subgingival end 236 of the core component 210 is mated to the implant -220, through the aperture 246, within the gingiva 242, at the junction of the gingiva 242 and the bone 240. The shape to be given to the aperture 246 through the gingiva 242 will depend on the type of tooth that was in the site where the implant 220 is now installed. An emergence-profiler healing component, which is described in reference to FIGS. 24-26, is then installed.

Figure 24:
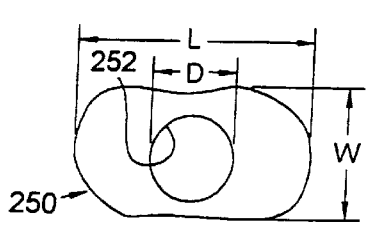
FIG. 24 is a top view of an emergence-profiler component used with the core abutment of FIGS. 22 and 23.

FIG. 24 illustrates a premolar-type emergence-profiler healing component 250 having a mesial-distal dimension "L" and a buccal-labial dimension "W" which are characteristic of that type. A hole 252 through this healing component 250 has essentially the same diameter "D" as the core component 210. In use, the healing component 250 is forced over the core component 210 so that the ribs 212 become embedded in the walls defining the hole 252 until the healing component 250 is seated on the shoulder 238. The assembly of both components may then be attached to the implant 220 in known fashion, using an abutment screw 254 having external threads mating with the internally-threaded bore of the implant 220. The core component 210 is thereby fixed on the implant 220, and the healing component 250 is thereby fixed non-rotatively on the core component 210. The opening of the core component 210 through which abutment screw 254 is placed is then closed by common methods.

FIG. 25 illustrates an alternative healing component 256 that can be used for restoration of another type tooth. In those cases where the healing component is not round (e.g: FIGS. 24 & 25) its orientation is automatically preserved in the impression. FIG. 26 illustrates a general-type healing component 260, which as shown is initially round in the shape of a truncated cone having the hole 252 through it. The initial shape of this component may be modified to a shape other than round. These healing components may be made of material allowing them to be modified at chair-side to a shape more nearly conforming to that of a particular tooth.

Figure 28:
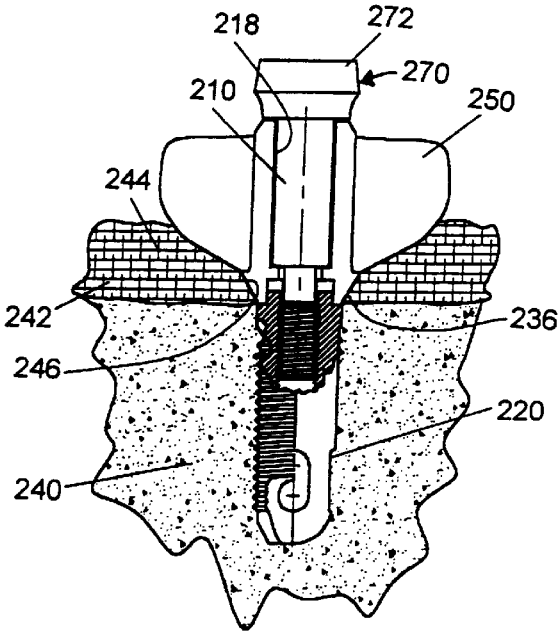
FIG. 28 shows a transfer coping utilizing the core component and emergence-profiler component according to the alternative embodiment of the invention.

As is apparent on FIGS. 27 and 28, a healing component, for example the component 250, is now fixed in a position to force the aperture 246 in the gingiva 242 to heal in a specified shape or contour. According to the present invention, after the healing process, when it is desired to take an impression for laboratory use, the abutment screw 254 is replaced with an impression coping screw 270. The impression screw 270 has an externally-threaded portion which mates with the internally threaded bore of the implant 220. The resulting assembly of the core component 210, healing component 250, and screw 270 then functions as a transfer coping which can be used with the closed tray or open tray method. A head 272 of the impression coping screw 270 is wider than the core component 210 and may be at least partly wider than the healing component 250, for latching the transfer coping in impression material (not shown). After an impression is made in a usual manner with the transfer coping in place on the implant 220, the entire assembly is removed from the implant 220 and attached to a laboratory analog of the implant 220 (not shown), and placed back in the impression, from which a stone model or the like can be made.

Since the gingiva tissue 242 will begin to close the formed opening 246 if the emergence-profiler element is removed for an extended interval of time, it is desirable to provide a keeper in the opening to preserve its shape. This can be done with a duplicate of the original core component 210 and the emergence-profiler healing component 250 (for example).

Alternatively, a simpler, and less expensive, keeper is illustrated in FIGS. 29–31. A keeper element 282, which may be made of an inexpensive plastic material, mimicking the shape of the original emergence-profiler component (e.g., component 250 in FIG. 24) which was removed, is carried on a sleeve 280 taking the place of the core component 210. The keeper element 282 includes a top surface 283. A cover screw 284 having a head which engages the top surface 283 completes the keeper element 282. The cover screw 284 is typically left in place while a restoration is being prepared.

FIG. 30 illustrates a modified keeper element 282' which has a turned-down upper surface 283'. The modified cover screw 284' has a corresponding mating edge that engages the turned-down upper surface 283'. FIG. 30 is indicative of modifications the dentist may perform on the keeper element 282 and cover screw 284.

As is indicated in FIG. 31, the sleeve 280 of FIG. 30 is eliminated and keeper element 286 is modified such that keeper element 286 can be made to perform the function of the sleeve 280. The keeper element 286 also includes a cover screw 284 which may be flush with the upper surface of the gingiva 242. The cover screw 284 engages the upper surface 289 of the keeper element 286.

What is claimed is:

1. A dental component for attachment to an implant implanted in living jawbone having overlying gingiva, said a gingival end near an interface of said gingiva and said jawbone, said dental component comprising:
    a body including a core and an emergence profiler element fitting over and engaging said core, said body having a gingival region extending through said gingiva for forming an aperture in said gingiva that exposes said gingival end of said implant;
    first means within said body for receiving a healing element, said healing element fastening said body to said implant so as to allow said gingiva to heal around said body for an extended period of time; and
    second means within said body for receiving an impression element, said impression element including an upper segment for extending above said body and receiving impression material, and a lower segment for securing said body to said implant.

2. The dental component of claim 1 wherein said core includes a plurality of ribs for non-rotationally engaging said emergence profiler element.

3. The dental component of claim 1 wherein said core includes a central bore extending therethrough, said central bore providing said first and second receiving means, said healing element being a screw having a head engaging a shoulder in said central bore, said impression element includes an impression receiving portion and an elongated screw holding said impression receiving portion on said body.

4. The dental component of claim 1 wherein said emergence profiler element is a polymeric material and said core is a metal.

5. The dental component of claim 1 wherein said core includes an internal surface defining a central bore extending therethrough, said central bore being said first and second receiving means, said internal surface including a Morse taper for engaging an outer surface with a corresponding Morse taper on said impression element.

6. The dental component of claim 1 wherein said emergence profiler element provides said outer surface of said body, said emergence profiler element being made of a material that is modifiable to conform to conditions at a site in which said emergence profiler element is installed.

7. The dental component of claim 1 wherein said core includes axial ribs and circumferential ribs to provide a surface to which said emergence profiler element is non-rotationally attached.

8. A dental system for use with an implant implanted at a site in living jawbone having overlying gingiva, said implant having a gingival end near an interface of said gingiva and said jawbone, said dental system comprising:
    a healing component having a lower end for engaging said gingival end of said implant and a gingival region extending through said gingiva for forming an aperture in said gingiva, said healing component including a bore extending therethrough; and
    an impression element to be partially disposed in said bore and mechanically coupled to said healing component, said impression element including a region for receiving impression material, said impression element and said healing abutment being retained by said impression material to develop a model of said site useful for fabricating an artificial tooth to be mounted on said implant.

9. The dental system of claim 8 wherein said bore includes a locking taper and said impression element includes a corresponding locking taper providing said mechanical coupling.

10. The dental system of claim 8 wherein said impression element includes an impression coping and an elongated screw.

11. A dental component for attachment to an implant implanted in living jawbone having overlying gingiva, said implant having a gingival end near an interface of said gingiva and said jawbone, said dental component comprising:
    an end surface to engage said gingival end of said implant;
    a gingival region with an outer surface for forming an aperture in said gingiva; and
    first and second internal tapered surfaces defining a bore, said first tapered surface of said bore adapted to receive a healing element that secures said body to said implant and allowing said gingiva to heal around said body for an extended period of time, said second tapered surface of said bore adapted to partially receive an impression element for engaging impression material, said first and second tapered surfaces tapering at different angles.

12. The dental component of claim 11 wherein one of said first and second tapered surfaces is angled so as to form a locking taper.

13. The dental component of claim 12 wherein said second surface is a frictionally locking taper for engaging a corresponding frictionally locking taper on an outer surface of said impression element.

14. The dental component of claim 13 wherein said frictionally locking taper is angled in the range from about 1° to about 5° from a central axis of said dental component.

15. The dental component of claim 11 wherein said dental component is a unitary member.

16. The dental component of claim 11 wherein said first and second surfaces are both angled at less than 90°0 with respect to a central axis of said dental component.

17. The dental component of claim 11 wherein said first surface is at an angle in the range from about 30° to about 60°.

18. The dental component of claim 11 wherein said first surface and second surfaces are immediately adjacent to each other.

19. The dental component of claim 11 wherein said bore being further defined by a nonround socket adjacent to said end.

20. The dental component of claim 11 wherein said outer surface is nonround in cross section.

21. A set of dental components for use with an implant implanted in living jawbone having overlying gingiva, said implant having a gingival end near an interface of said gingiva and said jawbone, said set of dental components comprising:
- a body having an end surface to engage said gingival end of said implant and an outer surface for forming an aperture in said gingiva, said body including first and second internal surfaces defining at least a portion of a bore that extends through said body;
- a healing screw for extending through said bore, said healing screw having a head for engaging said first internal surface of said body and a lower portion for threadably engaging a threaded bore within said implant; and
- an impression element distinct from said healing screw for extending through said bore, said impression element including a lower part for engaging said second internal surface of said body, said impression element having an upper segment for engaging impression material.

22. The set of dental components of claim 21 wherein said first internal surface is tapered and said head has a tapered surface for engaging said first internal surface.

23. The set of dental components of claim 21 wherein said first and second internal surfaces are tapered at different angles.

24. The set of dental components of claim 21 further including means for sealing a region between said internal surface and said head.

25. The set of dental components of claim 24 wherein said sealing means is an O-ring positioned between said head and said internal surface.

26. The set of dental components of claim 21 wherein said impression element includes an elongated screw having a wide head positioned above said body of said wide head being said upper segment for engaging said impression material.

27. The set of dental components of claim 21 wherein said impression element includes a coping bolt threadably engaging said implant and a coping head providing said upper segment for engaging said impression material, said coping head being held on said body by said coping bolt.

28. The set of dental components of claim 27 wherein said second internal surface has a frictionally locking taper, said coping head including an exterior surface having a corresponding frictionally locking taper, said frictionally locking tapers attaching said body to said coping head in response to said coping bolt being tightened.

29. The set of dental components of claim 27 wherein said coping head includes means for circumferentially orienting said coping head in said impression material.

30. The set of dental components of claim 29 wherein said coping head includes means for retaining said coping head and said body in said impression material.

31. A set of dental components for use with an implant implanted in living jawbone having overlying gingiva, said implant having a gingival end near an interface of said gingiva and said jawbone, said set of dental components comprising:
- a core having a lower surface for engaging said gingival end of said implant and an outer surface;
- a fastener holding said core on said implant;
- an emergence profiler element having an outer surface defining an outer contour for forming an aperture in said gingiva, said emergence profiler element having a hole extending therethrough for fitting around and mating with said core; and
- an impression element for attachment to a combination of said core and said emergence profiler element, said impression element having an upper segment for engaging said impression material.

32. The set of dental components of claim 31 wherein said core further includes on said outer surface means for restraining said emergence profile element from rotating therearound.

33. The set of dental components of claim 31 wherein said impression element includes an elongated, wide-headed impression-coping screw.

34. The set of dental components of claim 31 further including means on said outer surface of said elongated core for attaching said emergence profile elements thereon.

35. The set of dental components of claim 34 wherein said attaching means includes a plurality of ribs extending axially along said outer surface of said elongated core.

36. The set of dental components of claim 31 wherein said core has a central bore, said central bore receiving said fastener and a portion of said impression element.

37. The set of dental components of claim 36 wherein said core has a shoulder within said central bore, said fastener including a head engaging said shoulder.

38. The set of dental components of claim 31 wherein said emergence profiler element is made of plastic.

* * * * *

UNITED STATES PATENT AND TRADEMARK OFFICE
CERTIFICATE OF CORRECTION

PATENT NO.: 6,155,828
DATED: December 5, 2000
INVENTOR(S): Lazzara et al.

It is certified that errors appear in the above-identified patent, and that said Letters Patent is hereby corrected as shown below.

Column 11, Claim 1, line 27, after "said" insert --implant having--

Column 12, Claim 16, line 60, after "90°" delete "0"

Signed and Sealed this

Twenty-ninth Day of May, 2001

Attest:

NICHOLAS P. GODICI

Attesting Officer

Acting Director of the United States Patent and Trademark Office